(12) United States Patent
Canaud et al.

(10) Patent No.: US 7,794,422 B2
(45) Date of Patent: Sep. 14, 2010

(54) CATHETER PORT ASSEMBLY FOR EXTRACORPOREAL TREATMENT

(75) Inventors: Bernard Canaud, Montpellier (FR); John Stephens, Perkiomenville, PA (US)

(73) Assignee: Medical Components, Inc., Harleysville, PA (US)

( * ) Notice: Subject to any disclaimer, the term of this patent is extended or adjusted under 35 U.S.C. 154(b) by 1209 days.

(21) Appl. No.: 11/140,383

(22) Filed: May 27, 2005

(65) Prior Publication Data
US 2006/0271012 A1    Nov. 30, 2006

(51) Int. Cl.
*A61M 3/00*    (2006.01)
(52) U.S. Cl. .................................... 604/43; 604/288.01
(58) Field of Classification Search .................... 604/43, 604/108, 228, 246, 500, 284, 533–539
See application file for complete search history.

(56) References Cited

U.S. PATENT DOCUMENTS

| | | | | |
|---|---|---|---|---|
| 4,323,065 | A | * | 4/1982 | Kling ........................... 604/533 |
| 4,431,426 | A | * | 2/1984 | Groshong et al. ........... 604/523 |
| 4,434,810 | A | | 3/1984 | Atkinson |
| 4,578,063 | A | | 3/1986 | Inman et al. |
| 4,778,447 | A | | 10/1988 | Velde et al. |
| 5,098,406 | A | | 3/1992 | Sawyer |
| 5,284,475 | A | | 2/1994 | Mackal |
| 5,562,630 | A | | 10/1996 | Nichols |
| 5,613,655 | A | | 3/1997 | Marion |
| 5,676,346 | A | * | 10/1997 | Leinsing ................... 251/149.1 |
| 5,782,505 | A | | 7/1998 | Brooks et al. |
| 6,042,577 | A | * | 3/2000 | Chu et al. .................... 604/523 |
| 6,113,572 | A | * | 9/2000 | Gailey et al. .............. 604/93.01 |

(Continued)

FOREIGN PATENT DOCUMENTS

EP    0515 007 A1    11/1992

(Continued)

OTHER PUBLICATIONS

International Search Report, Application No. PCT/US04/04409, Mailed Jun. 6, 2005, 1 Page.

(Continued)

*Primary Examiner*—Nicholas D Lucchesi
*Assistant Examiner*—Gerald Landry, II
(74) *Attorney, Agent, or Firm*—Anton P. Ness, Esq.; Fox Rothschild LLP

(57) ABSTRACT

A catheter port assembly (100) having a body (101) having a distal end (110), a proximal end (120) and a longitudinal channel (116,124,136) extending therethrough is disclosed. The catheter port assembly further comprises a valve (150) disposed along the longitudinal channel. The valve (150) is adapted to restrict flow in at least one direction, and the distal end (110) is adapted to be connected to a catheter (200). The distal end (110) is adapted to be at least partially subcutaneously inserted into a patient after being connected to a catheter, and the proximal end (120) is adapted to be connected to an extracorporeal device. A distal cover (170) is disclosed to assure the connection of the port to the distal end of the catheter. Additionally, a bracket (190) is disclosed that stabilizes a plurality of catheter port assemblies after insertion into a patient. The present invention also discloses a method of inserting a catheter assembly comprising including the catheter port assembly.

15 Claims, 7 Drawing Sheets

U.S. PATENT DOCUMENTS

| | | |
|---|---|---|
| 6,190,371 B1 | 2/2001 | Maginot et al. |
| 6,193,697 B1 * | 2/2001 | Jepson et al. ............... 604/201 |
| 6,238,369 B1 * | 5/2001 | Burbank et al. .......... 604/93.01 |
| 6,299,131 B1 | 10/2001 | Ryan |
| 6,361,523 B1 | 3/2002 | Bierman |
| 6,364,869 B1 * | 4/2002 | Bonaldo ..................... 604/537 |
| 6,582,409 B1 * | 6/2003 | Squitieri ................ 604/288.01 |
| 6,585,705 B1 * | 7/2003 | Maginot et al. ............. 604/265 |
| 6,872,198 B1 | 3/2005 | Wilson et al. |
| 6,971,390 B1 * | 12/2005 | Vasek et al. ................. 604/533 |
| 7,048,717 B1 | 5/2006 | Frassica |
| 7,156,826 B2 * | 1/2007 | Ishii et al. ................... 604/256 |
| 7,331,613 B2 * | 2/2008 | Schulte ....................... 285/239 |
| 2003/0050610 A1 * | 3/2003 | Newton et al. ............... 604/256 |
| 2003/0088213 A1 * | 5/2003 | Schweikert et al. ......... 604/177 |
| 2003/0229313 A1 | 12/2003 | Bierman |
| 2004/0034329 A1 | 2/2004 | Mankus et al. |
| 2004/0059293 A1 * | 3/2004 | Chu et al. .................... 604/107 |
| 2004/0102738 A1 * | 5/2004 | Dikeman et al. ............ 604/256 |
| 2004/0193118 A1 | 9/2004 | Bergeron |
| 2004/0193119 A1 | 9/2004 | Canaud et al. |
| 2005/0251102 A1 * | 11/2005 | Hegland et al. ............. 604/500 |

FOREIGN PATENT DOCUMENTS

WO      WO 00/62844 A      10/2000

OTHER PUBLICATIONS

International Search Report, Application No. PCT/US05/18851, Mailed Dec. 30, 2005, 4 pages.

Written Opinion of International Searching Authority, PCT/US05/18851, Mailed Dec. 30, 2005, 3 pages.

Supplemental European Search Report, EP 04711257, dated Jun. 6, 2007 (3 pages).

\* cited by examiner

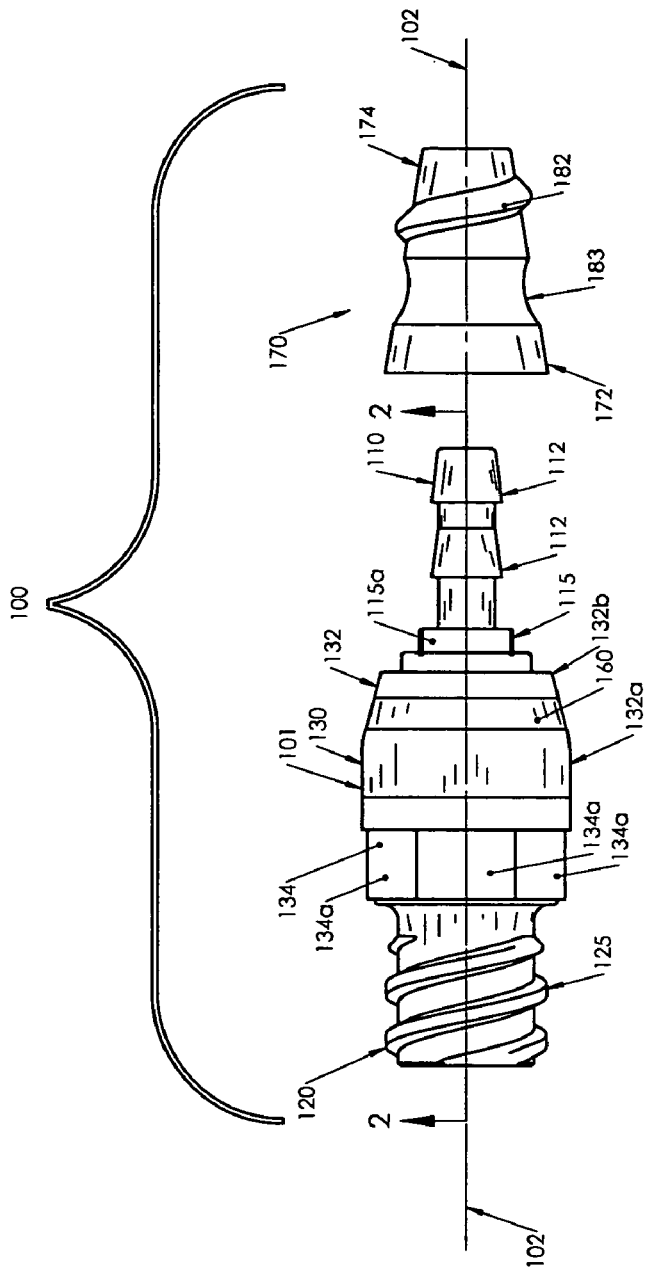
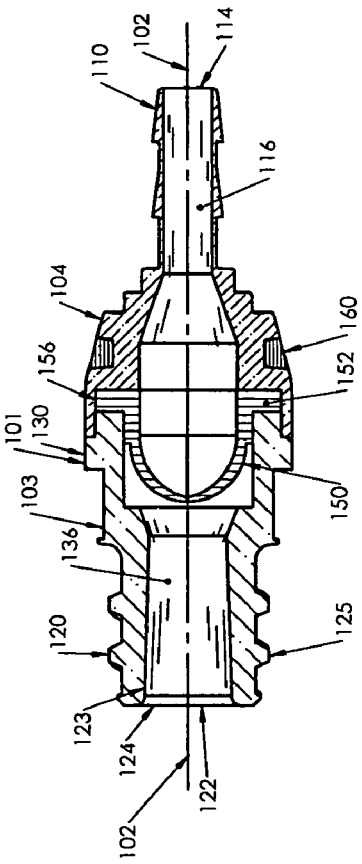
FIG. 1
FIG. 2

CATHETER PORT ASSEMBLY FOR EXTRACORPOREAL TREATMENT

FIELD OF THE INVENTION

The present invention relates to a catheter port assembly and a method of inserting the catheter port assembly.

BACKGROUND OF THE INVENTION

Catheters for extracorporeal blood purification may be located in various venous locations and cavities throughout the body of a patient for administration of solutes and for removal of toxins and fluids from the body via an extracorporeal blood circulation. Such venous catheterization may be performed by using a single catheter having multiple lumens. A typical example of a multiple lumen catheter is a dual lumen catheter in which one lumen serves to aspirate blood (arterial line) and the other lumen serves to restitute cleaned blood (venous line). An example of such a dual lumen catheter assembly is the SPLIT CATH® catheter, manufactured by Medical Components, Inc. of Harleysville, Pa. Catheterization may also be performed by using separate, single lumen catheters inserted through the same incision into the deep vein to be catheterized. Such dual catheter assemblies are also manufactured by Medical Components, Inc. of Harleysville, Pa. An example of a dual single lumen catheter assembly is the Tesio® catheter system, sold by Medical Components, Inc.

Generally, to insert any catheter into a deep vein or other blood vessel, the vessel is identified by aspiration with a long hollow needle in accordance with the well known Seldinger technique. When blood enters a syringe attached to the needle, indicating that the vessel has been found, a thin guide wire is then introduced, typically through the syringe needle or other introducer device into the interior of the vessel. The introducer device is then removed, leaving the distal end portion of the guide wire that has been inserted into the vessel within the vessel and the opposing proximal end of the guide wire projecting beyond the surface of the skin of the patient. At this point, several options are available to a physician for catheter placement. The simplest option is to pass a semi-rigid catheter into the vessel directly over the guide wire. The guide wire is then removed, leaving the catheter in position within the vessel. If the catheter to be inserted is significantly larger than the guide wire or is constructed from soft, flexible polymer material, a vein dilator device, generally within a sheath, is passed over the guide wire to enlarge the guidewire entrance site and to facilitate the introduction of the catheter. The dilator is removed and the catheter is inserted through the sheath over the guidewire, into the vein. The sheath is then removed, and the guidewire is also then removed, leaving the catheter in place.

For chronic catheterization, in which the catheter is intended to remain inside the patient for an extended period of time, such as for weeks or even months, it is typically desirable to subcutaneously tunnel the catheter into the patient using various tunneling techniques. The proximal end of the catheter may be tunneled after the catheter is inserted into the patient's vein. The subcutaneous tunnel provides a stable anchor to prevent the proximal end of the catheter from moving and possibly becoming dislodged, which could result in patient discomfort and risk of injury, such as infection, inflammation, or accidental withdrawal. Currently available products do not provide a catheter port that facilitates a secure connection with the exit site of the patient. Furthermore, current products do not provide for a compact port for the administration of extracorporeal treatment.

It would be beneficial to provide a catheter port assembly that provides a self-contained flow restricting valve. Additionally, it would be beneficial to provide a catheter port assembly that is adapted to be partially inserted into the exit site of a subcutaneous tunnel, thereby sealing the exit site and retaining the assembly partially within the subcutaneous tunnel through the ingrowth of flesh around the adapter.

BRIEF SUMMARY OF THE INVENTION

The present invention discloses a catheter port assembly having a body having a distal end, a proximal end and a longitudinal channel extending therethrough between the distal end and the proximal end. The catheter port assembly further comprises a valve disposed along the longitudinal channel. The valve is adapted to restrict flow in at least one direction. The distal end is adapted to be connected to a catheter. The distal end is also adapted to be at least partially subcutaneously inserted into a patient after being connected to a catheter and the proximal end is adapted to be connected to an extracorporeal device.

The present invention also discloses a catheter port assembly comprising a tubular body having a first end, a second end, a center portion and a longitudinal passageway extending between the first end and the second end. The catheter port assembly further comprises a valve disposed along the longitudinal passageway. The second end of the assembly comprises at least one barb adapted to be inserted within a catheter lumen, thereby engaging the catheter lumen. The center portion is wider than the catheter lumen. The second end further comprises a distal cover adapted to further engage the catheter lumen with the second end and provide a transition between the catheter lumen and the center portion. The second end is adapted to be partially subcutaneously inserted into a patient at a subcutaneous tunnel exit site.

The present invention also discloses a method of inserting a catheter port assembly. The method comprises providing a catheter, having at least one lumen, the at least one lumen of the catheter comprising at least one distal end and at least one proximal end. A trocar is also provided. The trocar includes a distal end and a proximal end. A suture having a first end and a second end, and a port assembly are also provided. The port assembly comprises a body having a distal end and a valve, and a distal cover. The method further includes inserting the distal end of the at least one lumen into a vessel of a patient, then connecting the proximal end of the at least one lumen and the first end of the suture, to the distal end of the trocar. The method further includes tunneling the trocar, the proximal end of the at least one lumen and the first end of the suture through the flesh of the patient to an exit site and pulling the proximal end of the at least one lumen and the first end of the suture at least partially through the exit site. Additionally, the method includes attaching the proximal end of the at least one lumen and the first end of the suture to the distal end of the body and pulling the second end of the suture until at least a portion of the assembly is disposed within the patient.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is an exploded side view of a preferred embodiment of a catheter port assembly according to the present invention.

FIG. 2 is a sectional view of a body of the catheter port assembly according to a preferred embodiment of the present invention.

FIG. 5a is a sectional view of the bracket of FIG. 5, taken along the line 5a-5a.

DETAILED DESCRIPTION OF THE INVENTION

Figure 3:
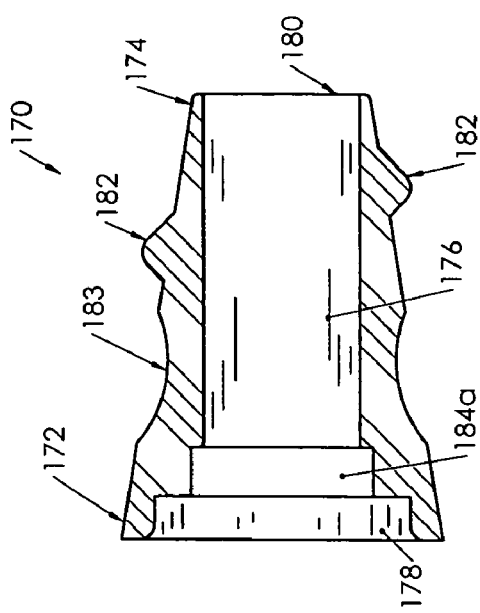
FIG. 3 is an enlarged sectional view of a distal cover of the catheter port assembly according to a preferred embodiment of the present invention.

In the drawings, like numerals indicate like elements throughout. Certain terminology is used herein for convenience only and is not to be taken as a limitation on the present invention. The words "proximal" and "distal" refer to directions away from and closer to, respectively, the insertion tip of the catheter in a catheter port assembly 100 according to the present invention. The terminology includes the words above specifically mentioned, derivatives thereof, and words of similar import. The following describes preferred embodiments of the invention. However, it should be understood, based on this disclosure, that the invention is not limited by the preferred embodiments described herein.

Referring now to FIG. 1, a catheter port adapter assembly 100 according to an embodiment of the present invention is shown. The assembly 100 has a body 101, comprising a distal portion 110 and a proximal portion 120. A longitudinal axis 102 extends between the distal portion 110 and the proximal portion 120. A central portion 130 is disposed along the longitudinal axis 102 between the distal portion 110 and the proximal portion 120. The assembly further comprises a distal cover 170.

In the preferred embodiment shown here, the distal portion 110 preferably is adapted to be inserted into a proximal end of a catheter lumen (not shown in FIG. 1). The distal portion 110 is adapted to engage the catheter lumen when the proximal end of the lumen is disposed about at least a portion of the distal portion 110. Preferably, the distal portion 110 comprises at least one barb 112 adapted to restrict the movement of the body 101 in a proximal direction relative to the lumen. While the at least one barb 112 is shown here comprises two barbs 112, those skilled in the art will recognize that movement of the catheter in relation to the body 101 may be restricted in other ways without departing from the scope of the present invention. Examples of such other means of attachment are a TESIO® style connection (disclosed in U.S. Pat. No. 5,624,413), a screw thread connection or any suitable combination of clips, couplings or fittings known to those skilled in the art to connect luers or adapters to catheter lumens. Alternatively, if the catheter being inserted is not retrograde subcutaneously tunneled, the catheter may be bonded to the assembly 100 or insert molded to the assembly 100.

Referring to FIG. 2, the distal portion 110 of the body 101 has a distal opening 114 and a distal passageway 116. The distal passageway 116 is adapted to facilitate the flow of liquids, preferably blood or medicaments, therethrough. Referring back to FIG. 1, preferably, a proximal part 115 of the distal portion 110, has a squared cross section, comprised of four flat sides 115a (only one side 115a being shown). Although the present embodiment discloses a proximal part 115 of the distal portion 110 having four sides, those skilled in the art will recognize that the proximal part 115 of the distal portion 110 may have any number of sides, or alternatively be rounded or any other suitable shape.

Referring to FIGS. 1 and 2, preferably, the proximal portion 120 is adapted to releasably connect to an extracorporeal treatment device, such as a hemodialysis machine (not shown), or a cap (not shown). In the present embodiment, the means for connection is a luer connection 122, which is well known to those skilled in the art. The luer connection 122 has a proximal opening 124 with a tapered inner wall 123. Preferably, male threads 125 are disposed on the outer surface of the proximal portion 120. Although male threads 125 and a luer connection 122 are shown here, those skilled in the art will recognize that the proximal end 120 may comprise any other suitable means of connecting the assembly 100 to an extracorporeal device.

Preferably, the central portion 130 has a larger cross section than either of the proximal or distal portions 120, 110 when taken along a plane perpendicular to the paper. Preferably, the central portion 130 has a generally circular cross section. The central portion 130 is sized to accommodate a valve 150 disposed therein along the longitudinal axis 102. Preferably, at least a portion of the central portion 130 has a tapered outer surface 132 that tapers from wider, at a proximal point 132a on the tapered outer surface 132, to narrower, at a distal point 132b on the tapered outer surface 132.

Referring back to FIG. 2, in construction, preferably the body 101 comprises at least a first body section 103, comprising the proximal portion 120 and a portion of the center portion 130, and a second body section 104, comprising the distal section 110 and a portion of the center portion 130. Preferably, the first body section 103 is adapted to engage and connect to the second body section 104. The connection may be welding, threads, a press fit or any other suitable means that is known to those skilled in the art. Preferably, a circumferential reveal 156 is formed between the first body section 103 and the second body section 104 when the first body section 103 and the second body section 104 are connected together. Preferably, during assembly, the valve 150 is disposed between the first body section 103 and the second body section 104 before the first body section 103 and the second body section 104 are connected together, thereby retaining the valve 150 therein. While the valve 150 is shown here retained between the first body section 103 and the second body section 104, those skilled in the art will recognize that many other means for retaining the valve 150 within the body 101 may be used without departing from the scope of the present invention.

Preferably, an indicator ring 160 is disposed about the outer surface of the central portion 130. In the preferred embodiment, the indicator ring 160 is disposed about the tapered outer surface 132 between the proximal point 132*a* and the distal point 132*b* of the tapered outer surface 132. Preferably, the indicator ring 160 is also tapered so that there is a smooth surface between the proximal point 132*a* and the distal point 132*b* of the tapered outer surface 132. Preferably, the indicator ring 160 is colored to indicate whether the lumen that the assembly 100 is attached to is a venous lumen, an arterial lumen, or used for some other purpose, such as delivering medicaments to the bloodstream. A color coded indicator ring 160 is desirable for the present invention because, when the assembly is properly installed in a patient, the lumen may be completely covered by the patient's flesh or the distal cover 170. The color coding system is well known to those skilled in the art. In the marking system, a blue marked lumen generally represents the venous lumen, or the lumen that facilitates the return of blood to the body, and the red marked lumen generally represents the arterial lumen, or the lumen that facilitates the withdrawal of blood from the body. Although an indicator ring 160 is used in the present embodiment to indicate the type of lumen that the assembly 100 is connected to, those skilled in the art will recognize that any other suitable means of identifying the lumens may be used as well.

The central portion 130 further preferably includes a flattened portion 134. Preferably, the outer surface of the flattened portion 134 has a hexagonal cross section comprised of six flattened sides 134*a* (only three sides 134*a* being shown). Preferably, the flattened portion 134 is disposed proximally of the tapered outer surface 132. While the preferred embodiment shown here discloses a flattened portion 134 having a hexagonal cross section, those skilled in the art will recognize that flattened portions 134 having any number of sides may be used without departing from the scope of the present invention. Alternatively, the flattened portion 134 may be oblong or some other shape as known to those skilled in the art.

Referring to FIG. 2, the central portion 130 and the proximal portion 120 define a central passageway 136 that extends from the proximal opening 124 to the distal passageway 116. Preferably, the central passageway 136 is generally tubular and extends along the longitudinal axis 102. Preferably, the valve 150 is disposed within the central passageway 136 along the longitudinal axis 102. Preferably, the valve 150 includes a retaining ridge 152. In the preferred embodiment, the retaining ridge 152 is at least partially disposed within the circumferential reveal 156 that extends around the central passageway 136. While in the present embodiment, the retaining ridge 152 is at least partially disposed within the circumferential reveal 156, thereby retaining the valve 150 within the assembly 100, those skilled in the art will recognize that the valve 150 may be retained within the assembly 100 by any other suitable means.

Preferably, the body 101 is constructed of stainless steel, titanium or some other suitable material.

Preferably, the valve 150 restricts flow in a first direction and facilitates flow in a second direction. It is also preferable that the valve 150 provides sufficient resistance to flow in all directions to reduce the occurrence of leakage of blood out of the patient or air or contaminants into the patient. The orientation of the valve 150 may be altered so that, in a pair of assemblies 100, the valve 150 of a first assembly 100 would restrict flow in a first direction and the valve 150 of a second assembly 100 would restrict flow in a second direction. The valve 150 shown in the present embodiment is a bidirectional pressure relief valve. Preferably, the valve 150 is constructed according to the teachings of U.S. Pat. No. 4,434,810. However, those skilled in the art will also recognize that the valve 150 may be a bidirectional valve (not shown), or any other suitable type of valve. Preferably, the valve 150 is constructed from silicone, a polymer or some other material.

Figure 4:
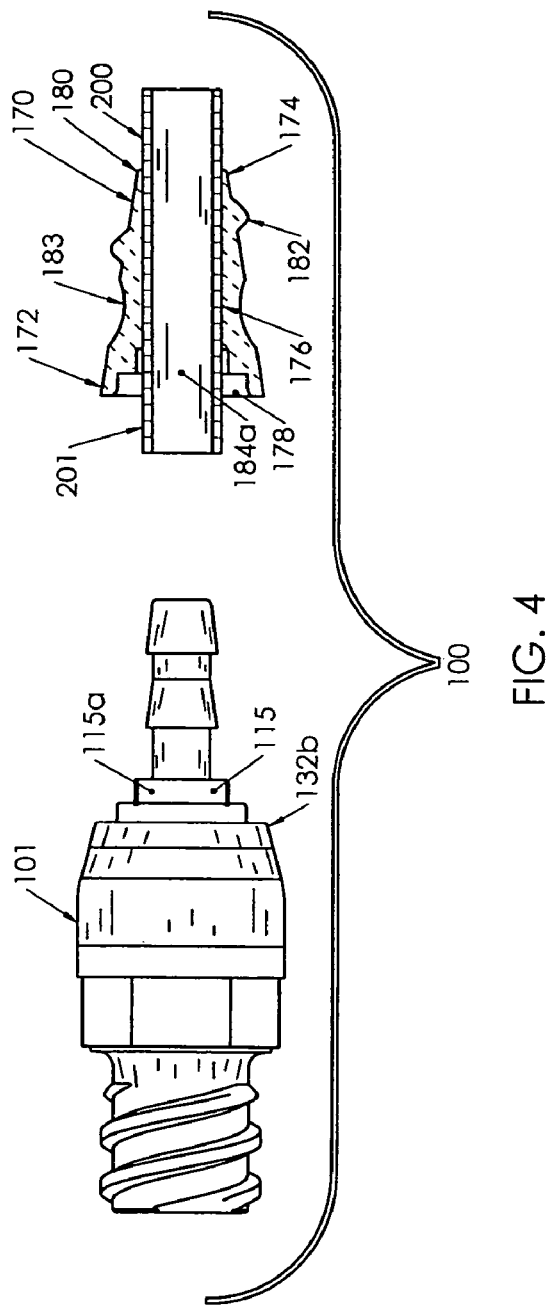
FIG. 4 is an exploded side view of a catheter port assembly, including a distal cover and catheter lumen, partially in section.

Referring to FIGS. 3 and 4, the assembly 100 further comprises the distal cover 170 having a proximal end 172, a distal end 174 and a longitudinal passageway 176 extending therethrough between the proximal end 172 and the distal end 174. The proximal end 172 of the distal cover 170 comprises a proximal opening 178. The distal end 174 of the distal cover 170 comprises a distal opening 180. The distal cover 170 is preferably conical in shape, having a widest part nearest the proximal end 172 and a narrowest part nearest the distal end 174.

The distal cover 170 is adapted to be connected to the body 101 by inserting the distal portion 110 of the body 101 through the proximal opening 178 of the distal cover 170. Preferably, the longitudinal passageway 176 of the distal cover 170 is sized to engage the body 101 and the outside of a catheter lumen 200 that is disposed over the distal portion 110 of the body 101.

Preferably, the proximal end 172 of the distal cover 170 is adapted to engage the four flat sides 115*a* of the proximal part 115 of the distal portion 110 of the assembly. The longitudinal passageway 176 of the distal cover 170 preferably comprises four flats 184*a* (only one flat 184*a* being shown) that frictionally engage the four flat sides 115*a* of the distal portion 110 of the body 101. Those skilled in the art will recognize that although four flat sides 115*a* and four flats 184*a* are shown here, any number of flat sides 115*a* and flats 184*a* may be used and that preferably, there is the same number of flat sides 115*a* and flats 184*a*.

Referring to FIG. 1, preferably the proximal end 172 of the distal cover 170 is sized so that widest part of distal cover 172 has a similar cross sectional size as the portion of the central portion 130 located at the distal point 132*b* on proximal outer surface 132. This facilitates a smooth transition between the proximal outer surface 132 and the distal cover 170 when the assembly 100 is assembled.

Referring now to FIGS. 1, 3 and 4, the distal cover 170 preferably comprises at least one retaining ridge 182. In the preferred embodiment shown here, the retaining ridge 182 is generally helical in shape and extends approximately 360 degrees around the distal cover 170. While a generally helical retaining ridge 182 is shown here, those skilled in the art will recognize that retaining ridges having various configurations may also be used without departing from the scope of the present invention. Preferably, the retaining ridge 182 is adapted to retain at least a portion of the assembly 100 within the flesh of a patient. Preferably, a rounded indentation 183 is circumferentially disposed around the distal cover 170 between the retaining ridge 182 and the proximal end 172. The rounded indentation 183 is preferably positioned along the distal cover 170 so that a part of the rounded indentation 183 will be disposed within the patient when the assembly is inserted and a portion of the rounded indentation 183 will remain outside of the patient after insertion. Preferably, the distal cover 170 is constructed from silicone, a polymer or some other material.

Figure 5:
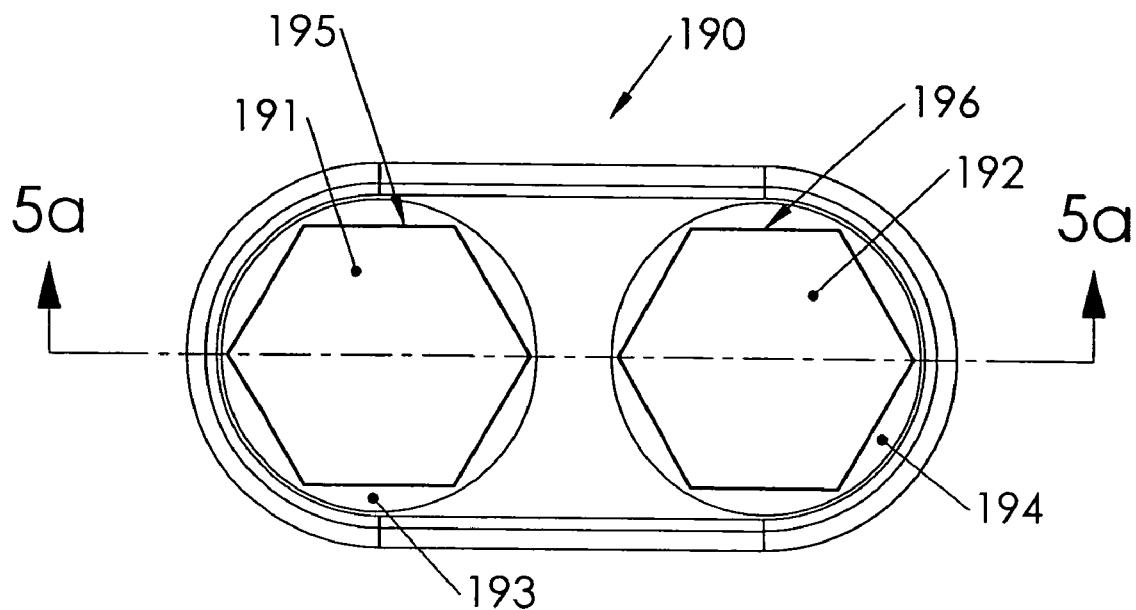
FIG. 5 is a front view of a bracket according to the preferred embodiment of the present invention.
Figure 5A:
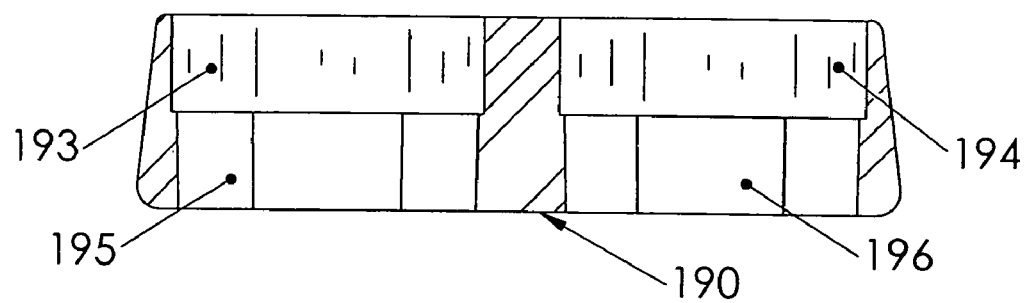
Figure 6:
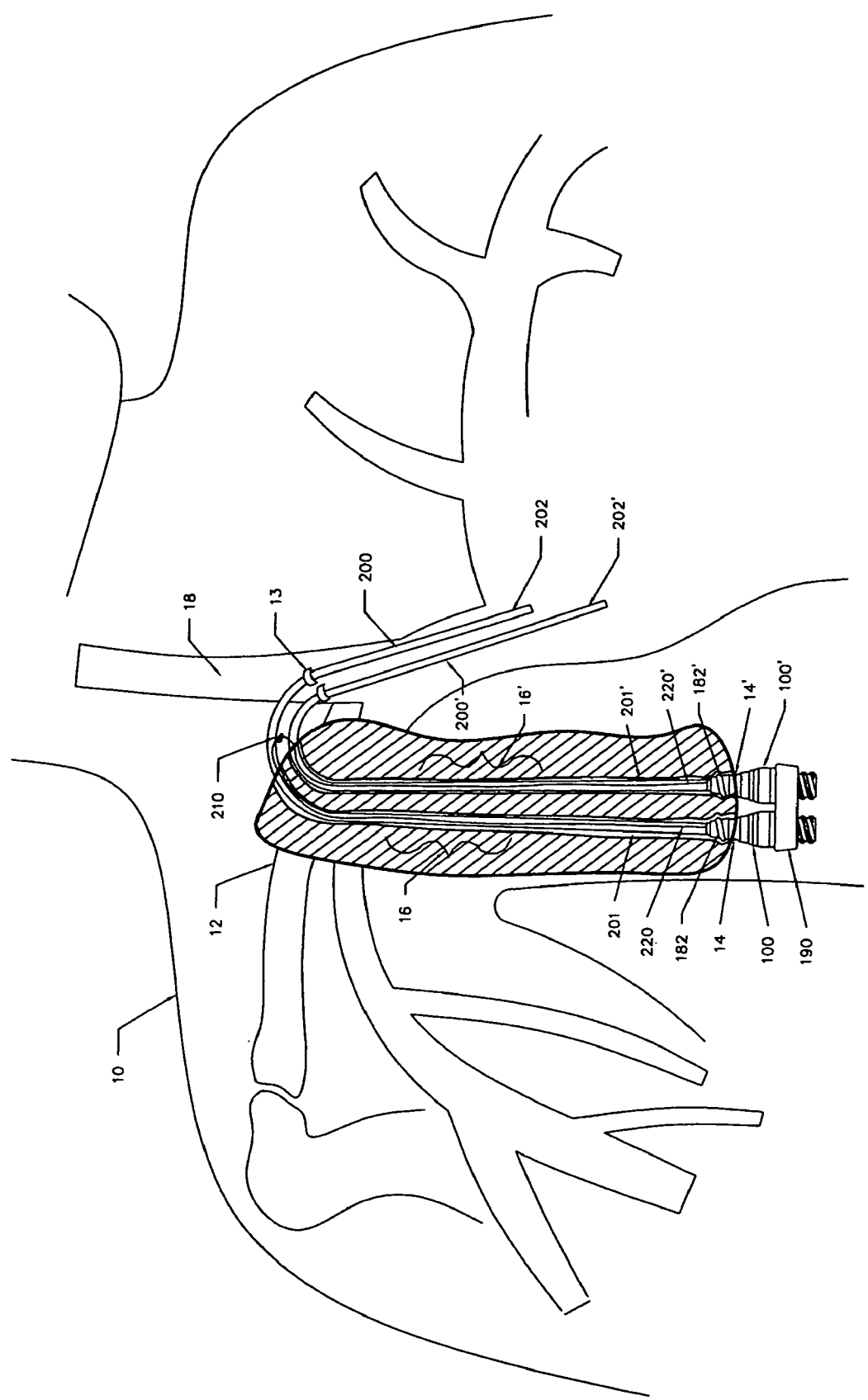
FIG. 6 is a partially broken away diagrammatic view of two catheter port assemblies subcutaneously tunneled and inserted into a patient according to the preferred embodiment of the present invention.

Referring to FIGS. 5, 5*a* and 6, a plurality of assemblies 100, 100' may be held together with a stabilizing bracket 190. Preferably, the bracket 190 is adapted to engage at least one assembly 100. The present embodiment shows a bracket 190 adapted to engage two assemblies 100, 100'. Preferably, the adapter 190 has a first passageway 191 and a second passageway 192, through which at least a portion of the assemblies 100 is to pass before the bracket 190 engages the assemblies 100. Preferably, the first and second passageways 191, 192 comprise first and second circular portions 193, 194 and first and second hexagonal portions 195, 196. Preferably, when the passageways 191, 192 of the bracket 190 engage the assemblies 100, 100', the circular portions 193, 194 are located distally of the hexagonal portions 195, 196 so that the circular portions 193, 194 engage the central portion 130 of the body 101 on each assembly 100, 100'. Preferably, when the bracket 190 engages the assemblies 100, 100', the hexagonal portions 195, 196 frictionally engage the flattened portion 134 of the body 101 on each assembly 100, 100'. The bracket 190 preferably engages the assemblies 100, 100' after the assemblies 100, 100' are inserted into the patient 10 preferably, after insertion, the bracket 190, with the side of the openings comprising the circular portions 193, 195 facing the patient, is slid distally about the assemblies 100, 100' until the circular portions 193, 194 engage each respective center portion 130 and the hexagonal portion engages each respective flattened portion 134.

Figure 5B:
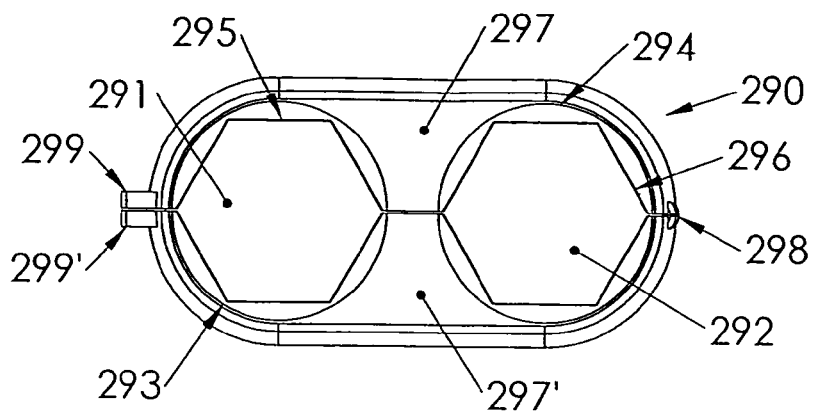
FIG. 5b is a front view of a bracket according to an alternative embodiment of the present invention.
Figure 5C:
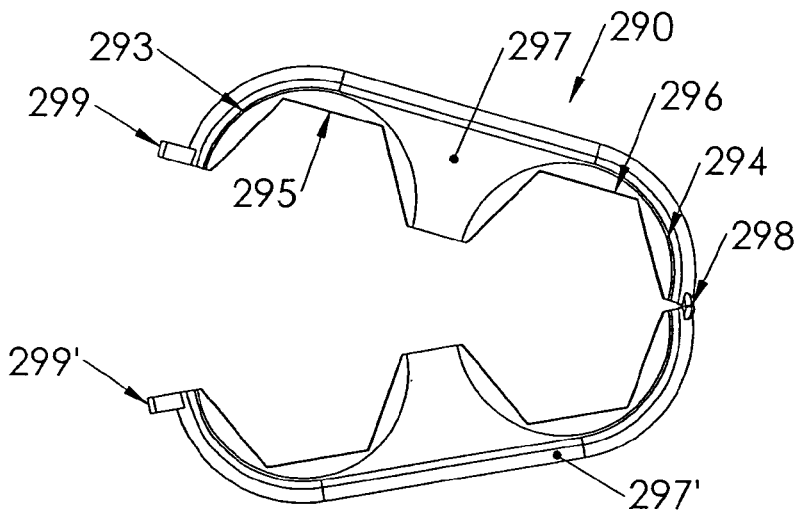
FIG. 5c is a front view of the bracket of FIG. 5b, in an open position.

Referring now to FIGS. 5b and 5c, an alternative bracket 290 is shown. Preferably, the bracket 290 has a first bracket portion 297 and a second bracket portion 297'. The first bracket portion 297 is preferably connected to the second bracket portion 297' by a hinge 298. Preferably, when the bracket 290 is disposed in the closed position, as shown in FIG. 5a, a first clasp portion 299 engages a second clasp portion 299', thereby retaining the bracket 290 in the closed position. Preferably, the first clasp portion 299 and second clasp portion 299' comprise a tang and a keeper respectively. Alternatively, the first and second clasp portions 299, 299' may comprise opposing tangs, a tab and a recess or any other configuration known to those skilled in the art to releasably retain the hinged bracket 290 in the closed position.

Like the bracket 190, the bracket 290 preferably comprises first and second passageways 291, 292 adapted to engage the assemblies 100, 100'. Preferably the passageways 291, 292 comprise first and second circular portions 293, 294 and first and second hexagonal portions 295, 296. Preferably, after the assemblies 100, 100' are inserted into the patient, the bracket 290 engages the assemblies 100, 100' by closing the bracket 290 around the assemblies 100, 100'. Preferably, like the bracket 190, when the bracket 290 engages the assemblies 100, 100', the hexagonal portions 295, 296 engage each respective flattened portion 134 and the circular portions 293, 294 engage each respective center portion 130 of the assemblies 100, 100'.

Figure 5D:
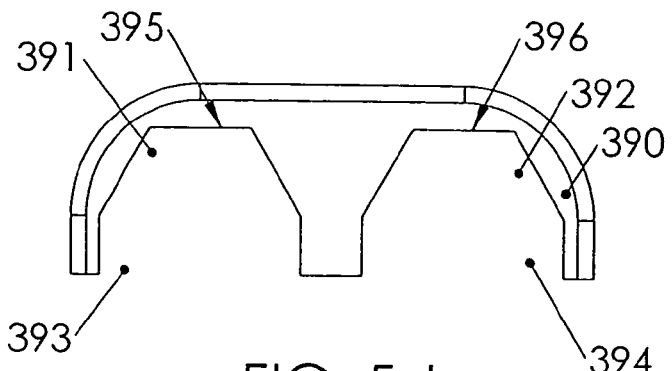
FIG. 5d is a front view of a bracket according a second alternative embodiment of the present invention.

A third embodiment of a bracket 390 is shown in FIG. 5d. The bracket 390 comprises a first and second openings 391, 392 respectively. Preferably, at least two edges of the first opening 391 and the second opening 392 respectively comprise first and second flattened bracket portions 395, 396. In the preferred embodiment shown in FIG. 5d, three sides of each of the first and second flattened bracket portions 395, 396 are generally similar to the upper half of a hexagon. Preferably, two opposing sides of each of the flattened bracket portions 395, 396 are generally parallel to each other and extend along the each side of the openings 391, 392 in a direction that is generally vertical when viewing FIG. 5d. The first and second flattened bracket portions are preferably adapted to engage each respective flattened portion 134 of the assemblies 100, 100'. Preferably, a first receiving end 393 and a second receiving end 394 are disposed on the opposite side of the first and second openings 391, 392 of the bracket 390 from the flattened bracket portions 395, 396. Preferably, the bracket is engaged to the assemblies 100, 100' by inserting the assemblies 100, 100' in the first and second receiving ends 393, 394, respectively, and then sliding the bracket 390 around the assemblies 100, 100' so that the first and second flattened bracket portions 395, 396 engage the flattened portion 134 of the assemblies 100, 100'.

Figure 5E:
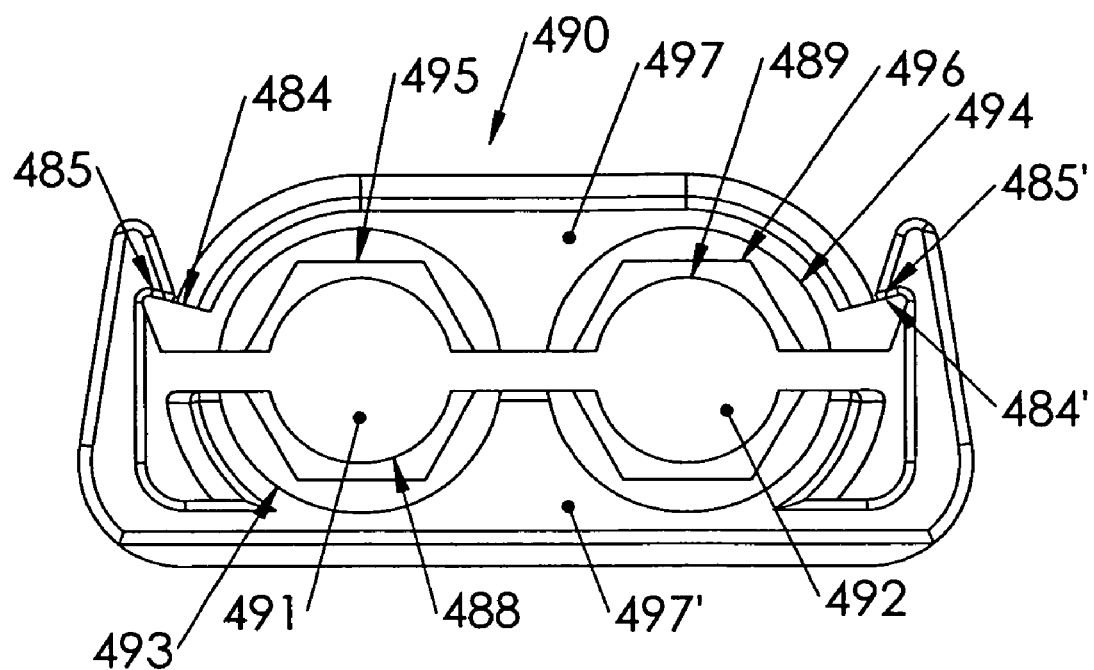
FIG. 5e is a front view of a bracket according to a third alternative embodiment of the present invention.
Figure 5F:
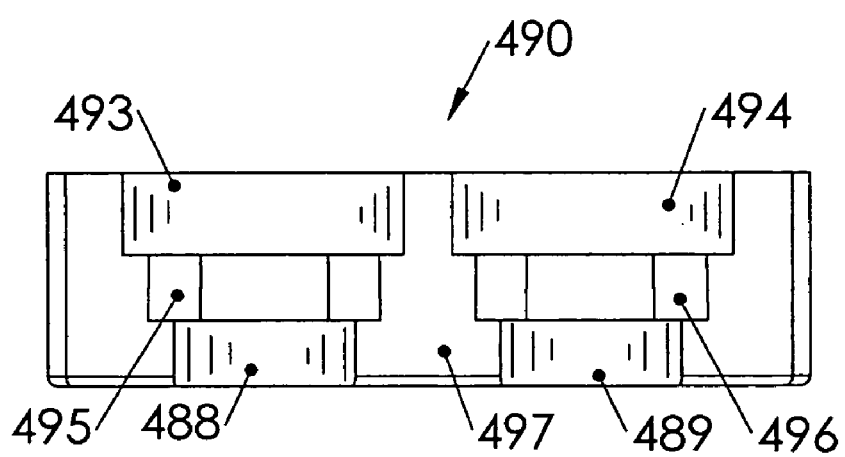
FIG. 5f is a bottom plan view of a portion of the bracket of FIG. 5e.

A fourth embodiment of a bracket 490 is shown in FIGS. 5e and 5f. The bracket 490 comprises a first bracket portion 497 and a second bracket portion 497'. Preferably the first and second bracket portions 497, 497' are similar to the first and second bracket portions 297, 297' of FIGS. 5b and 5c in that each of the first and second bracket portions 497, 497' define a portion of a first passageway 491 and a second passageway 492. Preferably the passageways 491, 492 comprise first and second circular portions 493, 494, first and second hexagonal portions 495, 496 and first and second narrowed portions 488, 489. Preferably, like the bracket 290, when the bracket 490 engages the assemblies 100, 100', the hexagonal portions 495, 496 engage each respective flattened portion 134 and the circular portions 493, 494 engage each respective center portion 130 of the assemblies 100, 100'. Preferably, the first and second narrowed portions 488, 489 are adapted to engage each respective proximal portion 120 of the assemblies 100, 100'. Preferably, the first and second narrowed portions 488, 489 engage the assemblies 100, 100' distally of each of the respective male threads 125 of each respective proximal portion 120 and proximally of the central portion 130.

Preferably, the first and second bracket portions 497, 497' are releasably connectable to each other via at least two tangs 484, 484' and clips 485, 485'. In the fourth embodiment shown in FIGS. 5e and 5f, the tangs 484, 484' extend outwardly from the sides of the first bracket portion 497 and the clips 485, 485' extend outwardly and towards the first bracket portion 497 from the second bracket portion 497'. Preferably, the clips 485, 485' are adapted to engage the tangs 484, 484' when the bracket 490 is disposed to frictionally engage the assemblies 100, 100'. The first bracket portion 497 is preferably disengaged from the second bracket portion 497' by pushing the clips 485, 485' away from each other and the first bracket portion 497.

Preferably the brackets 190, 290, 390, 490 are constructed from silicone, a polymer or some other suitable material. Alternatively, the brackets 190, 290, 390, 490 may be constructed of a combination of steel, titanium or some other rigid material and silicone, a polymer or some other suitable semirigid material.

Referring back to FIG. 6, two catheters 200, 200' are shown in an inserted position in a patient 10. The insertion is preferably performed one catheter at a time, however those skilled in the art will recognize that the catheters 200, 200' may be inserted simultaneously as well. The insertion of a catheter 200 according to the methods disclosed herein is performed in iterations. A first iteration comprises inserting a first catheter 200 and assembly 100 and a second iteration comprises inserting a second catheter 200' and assembly 100'. For each iteration, separate tools, equipment and accessories to complete the insertion are preferably provided. The separate tools, equipment and accessories preferably comprise at least the catheter 200, a trocar (not shown), a suture 220 and the port assembly 100. Those skilled in the art will recognize that more or less than two iterations may be performed without departing from the scope of the present invention.

For insertion, it is preferable to insert a distal end 202, 202' of the catheters into the patient's vessel 18, such as the patient's internal jugular vein. Insertion is preferably performed according to methods that are well known to those skilled in the art. After the distal ends 202, 202' are inserted into the vessel 18, the proximal ends 201, 201' are preferably connected to the distal (non pointed) end of the trocar using methods known to those skilled in the art. Preferably, a suture 220, 220' is attached to each of the trocars and subcutaneously tunneled with the catheters 200, 200' from an entrance site 13, located near where the distal end 202, 202' of the catheters 200, 200' enter the vessel 18, to exit sites 14, 14'. Preferably the catheters 200, 200' are tunneled through separate subcutaneous tunnels 16, 16'. Preferably, the sutures 220, 220' are attached to the trocars by tying the suture around the trocar, or by some other method known to those skilled in the art. Preferably, as shown in FIG. 6, the catheters 200, 200' are tunneled above the clavicle 12. Tunneling the catheters 200, 200' above the clavicle 12 provides additional anchoring and support, as is well known to those skilled in the art.

Preferably, the catheters 200, 200' are subcutaneously tunneled to a point where the proximal ends 201, 201' of the catheters 200, 200' exit the patient at exit sites 14, 14'. Preferably, the exit sites 14, 14' are larger than the outer diameter of the catheter 200, 200' but smaller than the outer diameter of the central portion 130 of the body 101.

Figure 7:
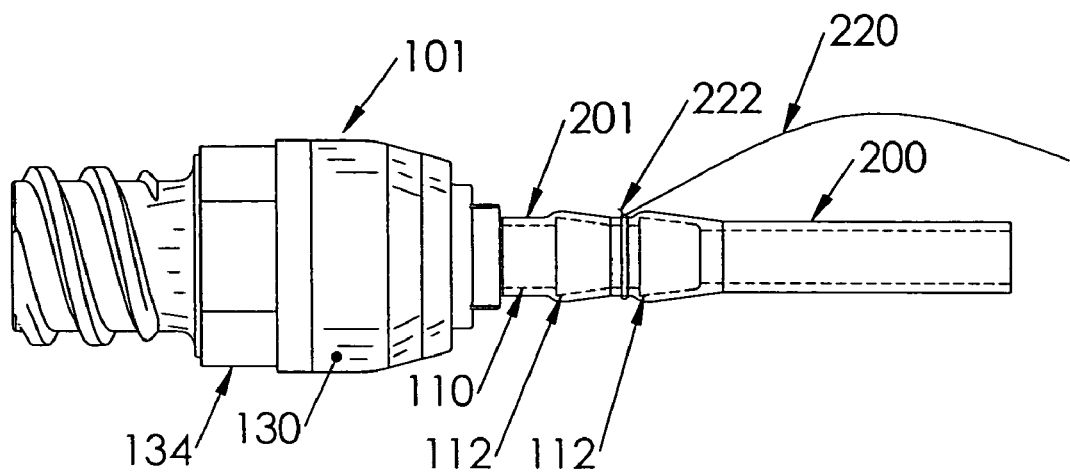
FIG. 7 is a side view of a catheter port assembly, including a catheter and a suture, according to the present invention.
Figure 7A:
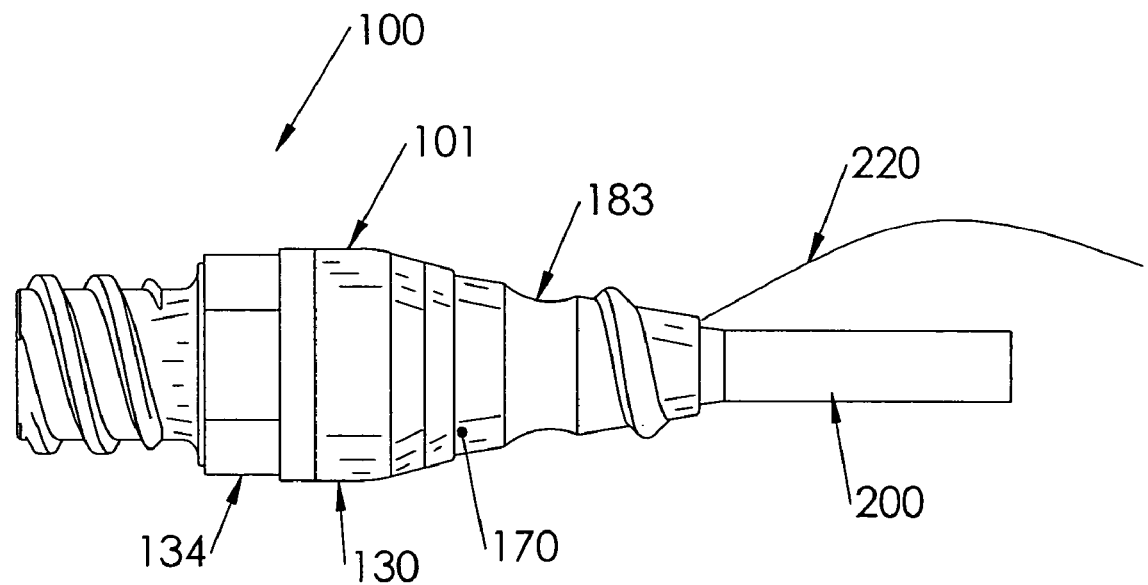
FIG. 7a is a side view of the catheter port assembly of FIG. 7, further including a distal cover, according to the present invention.

Referring to FIGS. 4, 7 and 7a, once the catheter lumen 200 is tunneled through the patient 10, and a portion of the catheter lumen 200 extends from the catheter exit site, the distal cover 170 is slid over a proximal end 201 of the catheter lumen 200, as shown in FIG. 4. Preferably, after the distal cover 170 (shown in FIGS. 4 and 7a) is placed over the catheter lumen 200, the proximal end 201 of the catheter lumen 200 is disposed around the distal portion of the body 101, as shown in FIG. 7. The proximal end 201 of catheter lumen 200 is preferably disposed about the barbs 112 when disposed around the distal portion of the body 101. Although the present embodiment shows a distal cover 170 that is slid over the lumen 200 prior to engaging the lumen 200 with the distal portion 110 of the assembly 100, those skilled in the art will recognize that, without departing from the scope of the present invention, the distal cover 170 may have some other configuration that allows the attachment of the distal cover 170 to the assembly at a time before or after said attachment occurs with the present embodiment.

Referring to FIG. 7, preferably, after the proximal end 201 of the catheter lumen 200 is slid over the distal portion 110 of the body 101, the suture 220 is tied, and knotted in a knot 222, around the proximal end 201 of the catheter lumen 200. Preferably, the suture 220 is tied around the catheter lumen 200 at a position along the distal portion 110 of the body 101 between two barbs 112. The catheter lumen 200 is further restricted from moving relative to the assembly 100 when the suture 220 is tightened around the catheter lumen 200, thereby squeezing the catheter lumen 200 around the distal portion 110 of the body 101.

Referring now to FIGS. 4, 7 and 7a, preferably, after the suture 220 is tightened around the catheter lumen 200, the suture 220 is placed along the catheter lumen 200 and the distal cover 170 is slid proximally along the catheter lumen 200, over the suture 220, toward the body 101. Preferably, the distal cover 170 is slid proximally until the distal cover 170 engages the body 101, thereby covering the proximal end 201 of the catheter lumen 200 and the knot 202 of the suture 200. As discussed previously, preferably, when the distal cover 170 is slid towards the body 101, the flats 184a of the distal cover 170 engage the flat sides 115a of the body 101.

Referring back to FIG. 6, after the assemblies 100, 100' are connected to the catheters 200, 200', the assemblies 100, 100' are then placed at least partially through the exit sites 14, 14' and into subcutaneous tunnels 16, 16'. When the assemblies 100, 100' are at least partially disposed within the exit sites 14, 14', preferably the retaining ridge 182, 182' of each assembly 100, 100' engages the flesh of the patient 10 so that the flesh of the patient 10 heals around the retaining ridge 182, thereby further securing the assemblies 100, 100' at least partially within the patient 10.

Referring to FIGS. 6, 7 and 7a, preferably, the catheter assemblies 100, 100' are pulled distally, back into the patient 10 until the assemblies 100, 100' are at least partially within the exit sites 14, 14'. Preferably, the assemblies 100, 100' at least partially plug the exit sites 14, 14' when pulled distally back into the patient 10. This is performed by pulling on the sutures 220, 220' at the entrance site 13. Preferably, the assemblies are pulled back into the patient to a point where the rounded indentation 183 is disposed at the skin level, leaving part of the rounded indentation 183 outside of the patient 10 and part of the rounded indentation 183 within the patient 10. Preferably, the retaining ridge 182 is disposed inside of the patient 10, thereby allowing the patient's 10 flesh to heal around the retaining ridge 182 and further restricting the movement of the assemblies 100, 100' relative to the patient 10. Preferably, the knot 222 of the suture 220 (shown in FIG. 7) is a first end of the sutures 220, 220' and second ends 224, 224' of the sutures 220, 220' are disposed near the entrance site 13 of the subcutaneous tunnels 16, 16' after the assemblies 100, 100' are tunneled. Preferably, after the inserting physician pulls on the second ends 224, 224' of the sutures 220, 220' thereby disposing the assemblies 100, 100' at least partially within the exit sites 14, 14', the second ends 224, 224' of the sutures 220, 220' are knotted together in a second knot 210, located near the entrance site 13. Knotting the sutures 220, 220' together near the entrance site 13 serves to further secure the assemblies 100, 100' within the patient 10.

Preferably, after the assemblies 100, 100' are inserted into the patient, the assemblies 100, 100' are secured to each other using the bracket 190. Preferably the bracket 190 engages the assemblies 100, 100' as discussed previously herein, although those skilled in the art will recognize that the bracket 190 may engage the assemblies 100, 100' in other ways without departing from the scope of the present invention.

In use, preferably the arterial assembly 100 is connected to the arterial blood line of an extracorporeal treatment device, such as a hemodialysis machine (not shown). The venous assembly 100' is then preferably connected to the venous blood line of an extracorporeal treatment device, such as a hemodialysis machine (not shown). During treatment, it is preferable that blood is withdrawn from the arterial lumen 200 and treated blood is returned to the vessel 18 via the venous lumen 200'. Preferably, the respective valves 150 are adapted to facilitate the direction of blood flow preferred for each lumen 200, 200'. Preferably, each respective valve 150 is adapted to facilitate flow therethrough even if the assemblies 100, 100' are not connected to the proper extracorporeal bloodlines. In a situation involving improper connections, it is preferable that each respective valve 150 would allow flow at decreased levels, and that in a case of disconnection, each respective valve 150 would restrict the flow of blood, air or contaminants therethrough.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A catheter port assembly comprising:
a catheter having a proximal catheter portion concluding in a proximal catheter end and being adapted for implantation into vasculature of a patient and subcutaneous tunneling of the proximal portion; and
a port body having an open distal end, an open proximal port end and a longitudinal channel extending therethrough between the open distal end and the open proximal port end, the open proximal port end being adapted to be mechanically releasably coupled to an extracorporeal device;
the port body further comprising a valve enclosed therein and disposed along the longitudinal channel;
wherein the valve is adapted to restrict flow in at least one direction;
wherein the distal end is adapted to be connected to the proximal end of the subcutaneously tunneled proximal catheter portion;
wherein the distal end is further adapted to be at least partially inserted into an exit of the subcutaneous tunnel of the patient after being connected to the catheter; and
wherein the proximal port end is externally exposed at the exit to be coupled to the extracorporeal device.

2. The catheter port assembly according to claim 1, wherein the distal end further comprises a cover adapted to further connect the catheter to the distal end.

3. The catheter port assembly according to claim 2, wherein the distal cover is frustoconical.

4. The catheter port assembly according to claim 2, the distal cover further comprising at least one external retaining ridge proximate a distal end thereof, whereby the cover is adapted to retain itself in the tunnel exit as remaining portions of the port extend proximally therefrom outside the patient.

5. The catheter port assembly according to claim 2, wherein the distal cover is sized to at least partially fit within the exit site of a subcutaneous tunnel.

6. The catheter port assembly according to claim 1, wherein the proximal port end comprises a luer connection.

7. The catheter port assembly according to claim 1, wherein the catheter is further connected to the distal end by a suture.

8. The catheter port assembly according to claim 1, wherein the distal end further comprises at least one barb.

9. A catheter port assembly comprising:
a catheter having a proximal catheter portion concluding in a proximal catheter end and being adapted for implantation into vasculature of a patient and subcutaneous tunneling of the proximal portion;
a tubular body having an open first end, an open second end, a center portion and a longitudinal passageway extending between the open first end and the open second end, and the open first end being adapted to be mechanically releasably coupled to an extracorporeal device;
a valve enclosed within the tubular body and disposed along the longitudinal passageway;
wherein the second end of the assembly comprises at least one barb adapted to be inserted within a lumen of the catheter, thereby engaging the catheter lumen;
wherein the center portion is wider than the catheter lumen;
wherein the second end further comprises a distal cover adapted to further engage the catheter lumen with the second end and provide a transition between the catheter lumen and the center portion; and
wherein the second end is adapted to be partially subcutaneously inserted into a patient at an exit site of the subcutaneous tunnel while the open first end remains externally exposed for coupling to the extracorporeal device.

10. The catheter port assembly according to claim 9, wherein the assembly is adapted to plug the exit site of the subcutaneous tunnel.

11. The catheter port assembly according to claim 9, the distal cover further comprising at least one external retaining ridge proximate a distal end thereof, whereby the cover is adapted to retain itself in the tunnel exit as remaining portions of the port extend proximally therefrom outside the patient.

12. The catheter port assembly of claim 4, wherein the retaining ridge is helical.

13. The catheter port assembly of claim 11, wherein the retaining ridge is helical.

14. The catheter port assembly of claim 1, wherein the valve is affixed within the port body.

15. The catheter port assembly of claim 9, wherein the valve is affixed within the port body.

* * * * *